United States Patent [19]
Portmann et al.

[11] Patent Number: 5,789,242
[45] Date of Patent: Aug. 4, 1998

[54] METHOD AND DEVICE FOR DETERMINING TOXICITY AS WELL AS THE USE THEREOF

[75] Inventors: Rudolf Portmann, Bern; Mathias Leumann, Weisslingen; Stefan Thommen, Kloten, all of Switzerland

[73] Assignee: Schweizerische Eidgenossenshaft Vertreten Durch Das AC-Laboratorium Spiez Der Gruppe Rustung, Spiez, Switzerland

[21] Appl. No.: 716,163

[22] PCT Filed: Mar. 13, 1995

[86] PCT No.: PCT/CH95/00055

§ 371 Date: Sep. 18, 1996

§ 102(e) Date: Sep. 18, 1996

[87] PCT Pub. No.: WO95/25955

PCT Pub. Date: Sep. 28, 1995

[30] Foreign Application Priority Data

Mar. 19, 1994 [CH] Switzerland ............... 811/94

[51] Int. Cl.⁶ ............... C12M 1/34; C06K 9/00; C06K 9/36; C12N 5/00
[52] U.S. Cl. ............... 435/288.7; 435/287.2; 435/325; 435/404; 435/32; 382/133; 382/6; 382/107; 382/110; 382/128; 382/156; 382/160; 382/165; 382/194; 382/237
[58] Field of Search ............... 382/133, 6, 107, 382/110, 128, 156, 160, 165, 194, 237; 435/287.2, 288.7, 325, 404, 32

[56] References Cited

U.S. PATENT DOCUMENTS 4,856,073 8/1989 Farber et al. ............... 382/6

FOREIGN PATENT DOCUMENTS

| 2906194 | 8/1980 | Germany | G01N 33/18 |
| 3345196 | 7/1985 | Germany | |
| 3922358 | 1/1991 | Germany | G01N 33/18 |
| WO 901286 | 11/1990 | WIPO | |
| WO9012886 | 11/1990 | WIPO | C12Q 1/00 |

OTHER PUBLICATIONS

Vol. 62 Rev. Sci Instrum. Three Dimensional Recording and Measurement... S. Baba et al pp540–541 (Feb. 1991).

WPI/Derwent Abstracts A.P. Eskov et al., Water Toxic Monitor... — SU1677630.

Patent Abstracts of Japan — JP 1047950. S. Isao. Identification And Separation Method... Pub Feb. 22, 1989.

*Primary Examiner*—W. Gary Jones
*Assistant Examiner*—Dianne Rees
*Attorney, Agent, or Firm*—Schweitzer Cornman Gross & Bondell LLP

[57] ABSTRACT

The invention concerns a method for determining the toxicity of water-soluble substances or of substances which can be mixed with water and thus obtaining quantitative information concerning the toxic effect of said substances. The invention helps to reduce the number of tests, necessary hitherto, performed on mammals. According to the method, at least two measurements determine the variation in mobility and/or size of test organisms in an aqueous medium, under the influence of at least one toxic substance. A device for carrying out the method comprises an image-detection unit which detects the object and sequentially records images of this object in at least one plane at predetermined time intervals. Arranged downstream of the image-detection unit is an evaluation arrangement with a computer and display devices which statistically evaluate the mobility and/or size of the organisms in relation to the existing toxicity. The method is used in particular for determining toxic influences on the environment, in particular water fauna, and for determining side-effects and contraindications of pharmaceuticals and foodstuffs.

7 Claims, 12 Drawing Sheets

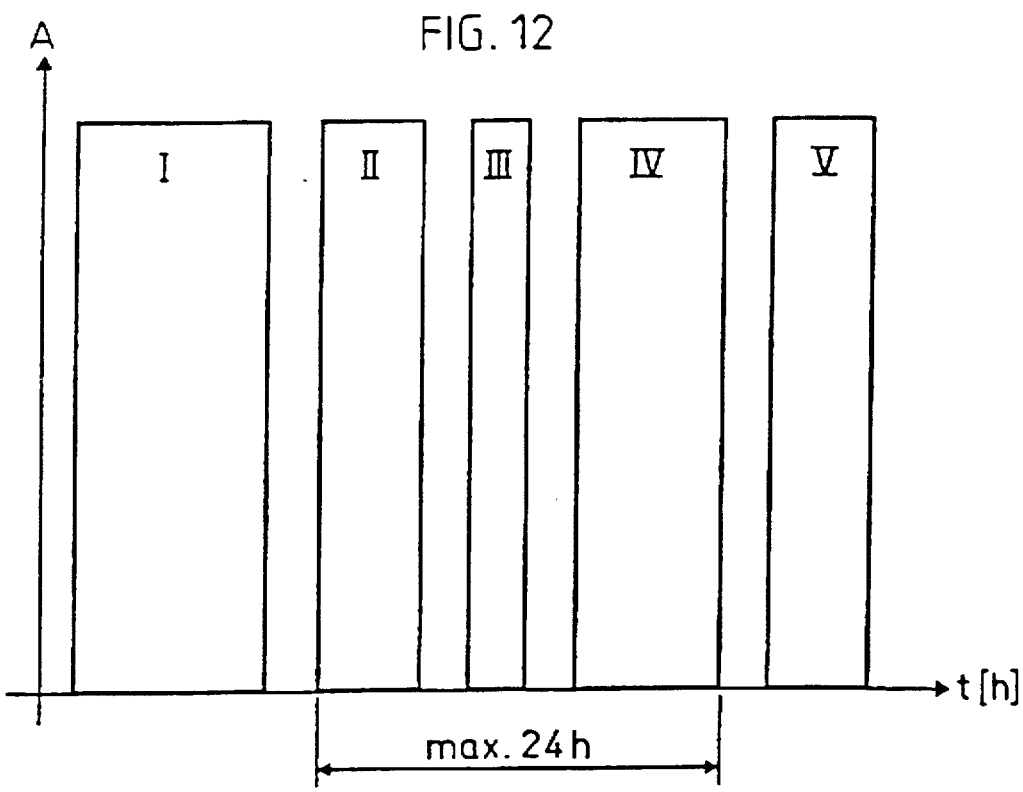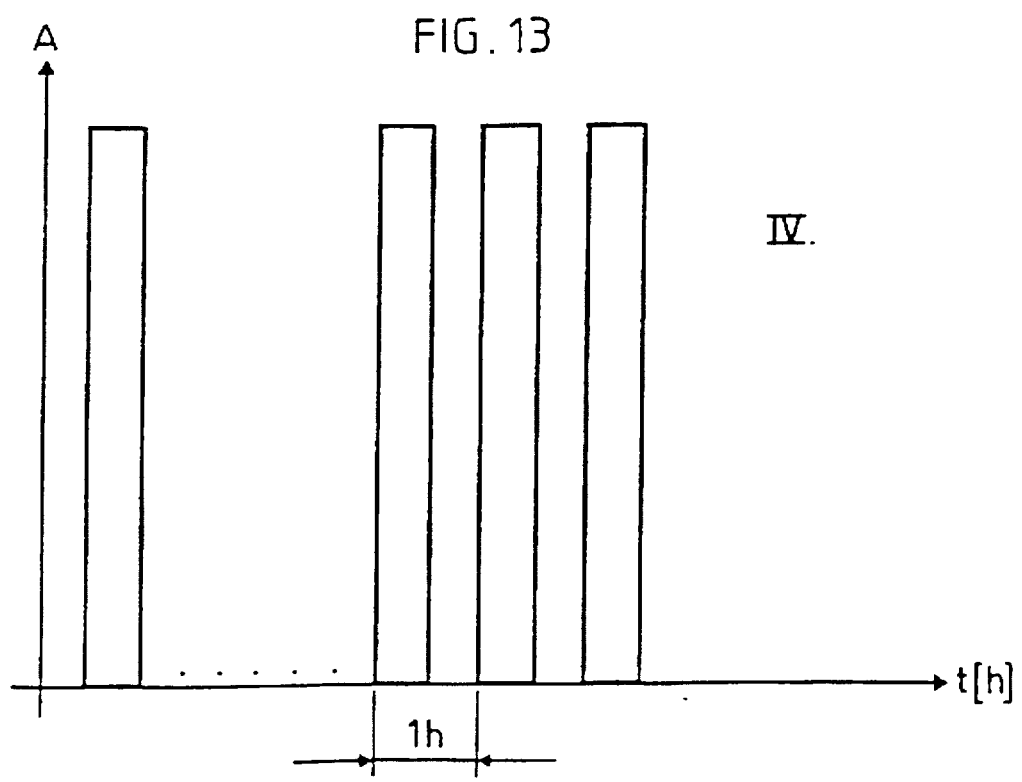

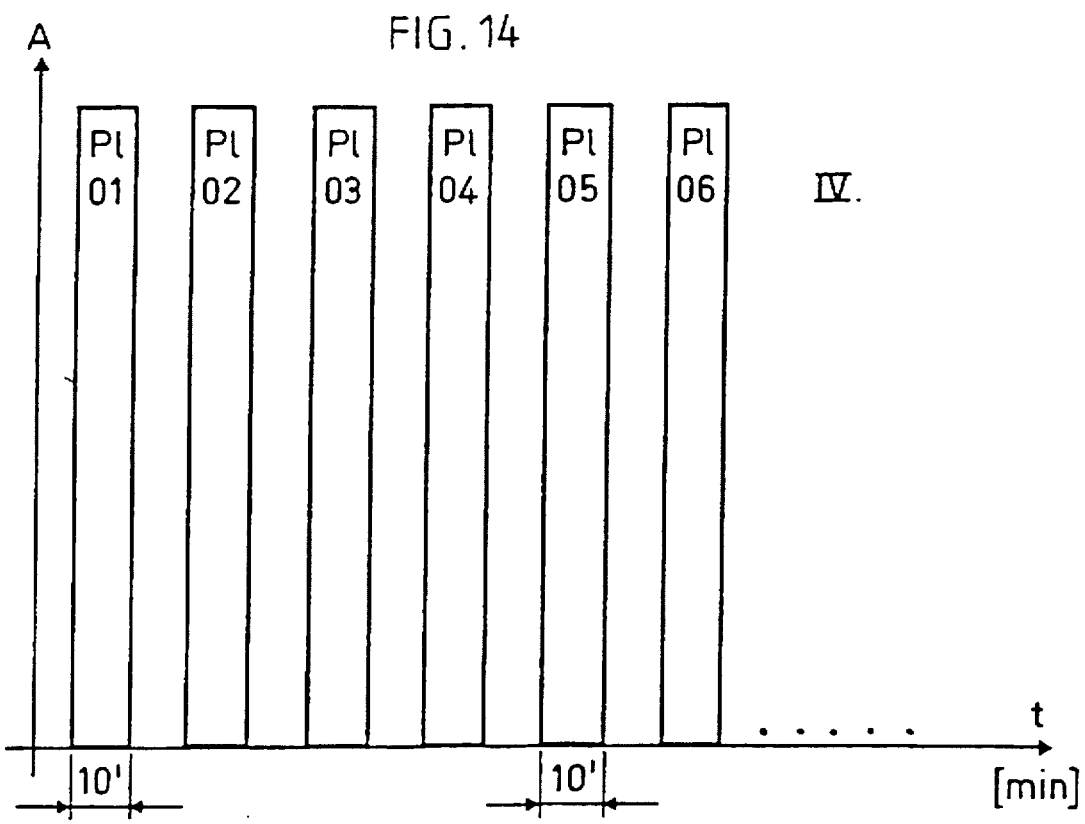
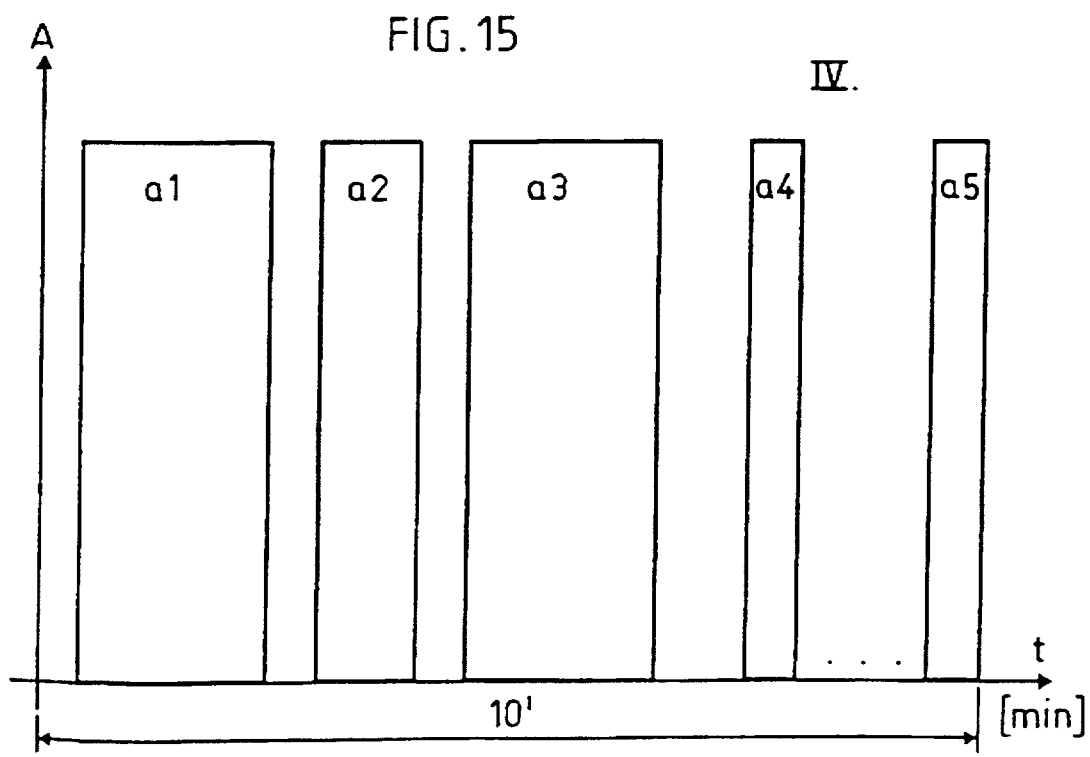

METHOD AND DEVICE FOR DETERMINING TOXICITY AS WELL AS THE USE THEREOF

The invention relates to a method for determination of the toxicity of substances soluble in, or miscible with, water.

The invention equally relates to a suitable device for carrying out the method, as well as an application thereof.

BACKGROUND OF THE INVENTION

It is well known that, under the effect of toxic substances, the vitality of organisms is impaired. While this is enough to give proof of the presence of such substances, it does not permit conclusions to be drawn concerning the degree of toxicity and/or concerning the substance.

It is thus an object of the invention to provide a method that facilitates a quantitative statement concerning the toxicity of substances and that at least contributes to a reduction of the still common, time-consuming experiments using mammals within the framework of essential safety tests.

It is a further object to provide a device permitting the method to be automated, its evaluation to be rationalized and authentically documented.

SUMMARY OF THE INVENTION

According to the invention, this is achieved by detecting a change in the mobility and/or in the size of at least two individuals of a single type of test organism in an aqueous medium under the effect of at least one toxic substance during at least two intervals of time, with at least one reference measurement and at least one further measurement being carried out after the admixture of the toxic substances. The concept "mobility" was adopted from solid-state physics and describes the "movement activity" and, in particular, the "mobility" of the test organisms which, in aqueous media, is simply observed as their "shift of location" per unit time.

This mobility can however also be perceived by observing the function of specific organs of the test organism.

An elevated frequency of the mobility of single organs permits conclusions to be drawn concerning a specific toxicity, without the resulting "shift of location" of the organisms being necessarily affected.

With substances inhibiting cell growth, observation or measurement of the size of the test organisms as a function of time constitutes a measure of this specific type of toxicity.

Toxicity determinations of this sort can be carried out in parallel with mobility determinations, but also separately therefrom, with the same instrumental means.

According to the invention, it is possible to use microorganisms for the determination of toxicity of substances by measuring the effect of single substances or of combinations of substances on the changes in these organisms. Such measurements allow the necessary amount of experiments on pain-perceptive laboratory animals to be massively reduced.

To increase the significance of the measurements, it is the preferred practice to observe a plurality of groups of identical test organisms separated from one another and to collectively evaluate each group.

A further advantage of the method resides in its simplicity and facile applicability, as well as in its low costs.

The concept of toxicity is, however, not limited to the effect of poison in the conventional sense; it can be expanded to apply to any perceptible effect (reaction) on a living organism.

The device for carrying out the method is characterized in that an image acquisition unit is provided which, in predeterminable time intervals, carries out object recognition and a sequential recording of the object position in at least one plane, that the image acquisition unit is associated with an evaluation arrangement including a computer and display means which, in relation to the toxicity present, carry out a statistical evaluation of the mobility of the organisms.

In the most simple case, the image acquisition unit is designed to be mechanically displaceable and is guided over the samples to be examined.

A change in mobility is expressed by a distance traversed per unit time by the test organism.

Significant values of mobility can be derived from acceleration.

The toxicity calculated according to the invention is a relative toxicity, related to a standard toxicity.

Determination of the movement velocity as well as the calculation of the resulting acceleration values and/or of the changes in the size of the organisms can be performed in a plane as well as three-dimensionally, depending on the refinement of the apparatus used. From these results it is possible in the simplest manner to plot characteristic curves interpretation of which can be made to indicate the effect of substances also on higher organisms.

The invention is advantageously applied using lower organisms as test organisms. Particularly suitable for this purpose are organisms living in water, as their mobility is most easily observable.

Performance of the test using Artemia salina Nauplia is affected neither by seasonal dependencies nor by feeding and breeding, but by ambient temperature and the time factor, so that only automated processes are suitable as professional investigation means.

According to experience, an increase in ambient temperature relative to normal temperature results in an increase in the mobility of the test organisms.

In order to obtain reproducible results, it is recommended to carry out, and normalize, the tests at 22° C.±1° C. Using conventional apparatus, this value is maintained constant with relative ease and, moreover, prevents excessive evaporation and water vapor formation with extended observations.

Under unfavorable conditions of life, Artemia salina forms cysts (eggs that are arrested in the early gastrula stage) and can thus be preserved over many years.

It is thus most advantageous to carry out the tests in sea-water, using such Euphyllopoda as Artemia salina Nauplien (in embryonic stages 3 and 4, at a size of about 0.9–1.15 mm).

Also applicable are freely swimming Rotatoria (Ploima).

For special investigations, i.e., when testing carcinogenic substances, water-fleas (Cladocera) are the preferred species, as they enable in a simple way to conduct observations over two generations.

Since Artemia salina is a sea-water organism, artificial sea-water is an adequate ambience for measurements.

In order to preclude possibly uncontrolled reactions between the toxic substance and sea-water and/or tap water, it may be advantageous to use fresh-water types of the Euphyllopoda in artificial fresh water consisting of distilled water with sodium bicarbonate. Equally recommended is the use of artificially produced sea-water.

According to the invention, other organisms, too, can be used, e.g., tadpoles etc.

Determination of the mobility of the test organisms can be effected in a purely optical way with the aid of a microscope, a slowing-down of the mobility and/or an inactivation of the test organism being observable under the effect of the toxic substance.

Although in case of a small number of samples measurements with a microscope are definitely possible, for reasons of reliability and standardization to be aimed at, it is already at this point recommended to use automated testing equipment.

In a preferred embodiment of the method, measurement is carried out using a micro-titration tray, for instance such as described in detail in U.S. Pat. No. 5,540,891 of Jul. 30, 1996.

For the preferred electrooptical instrumental analysis, the water-soluble substances to be investigated are dissolved in water or in artificial sea-water, are introduced into the above-described receptacles, the test organisms are added, and their reaction is electronically evaluated.

In the course of the analysis, the change in the mobility of the test organism per receptacle is averaged and compared with earlier recorded values. Appropriate correlations yield quantitative statements concerning the toxicity present.

The above investigations should always be carried out under identical conditions, since the result is affected by temperature.

The course of the method can be significantly optimized by systematic, pipette-assisted admixture, thereby largely eliminating potential error sources.

The device provided for carrying out the method facilitates a simple evaluation of the observed images by conventional EDV-means. By the forming of quotients, of all distances covered per time interval and per image, a relative mean velocity can be determined and, by means of the second derivative, also the acceleration values thereof.

Of particular importance is the establishing of a distinction between moving and nonmoving objects as, on the one hand, many of the test organisms shed their skins during the observation period, with the discarded skins being liable to cause spurious recordings; on the other hand, the already dead organisms must be detected and eliminated from the calculation.

Particularly suitable for carrying out the method is a so-called CCD-shutter camera, as at present it is only cameras of this type that are capable of delivering sharp and interpretable images.

By means of the arrangement including two cameras, it is possible to observe and measure the movements of the test organism also in three dimensions.

Given a sufficiently large investment in apparatus, i.e., given the use of appropriate cameras and sufficiently large image data memories as well as sufficiently fast computers, it is in principle possible to simultaneously record, and separately assess, all test organisms of a test setup.

A rational, automated observation and evaluation of test organisms can be realized provided the transport mechanism used works smoothly.

The applications for the invention may relate to actual needs of environmental protection, foodstuff technology, and the pharmaceutical industry. Clearly, further applications can be thought of which also relate to other areas of biology.

Determination of toxicity, as thoroughly tried out with Artemia salina Nauplien, facilitates clarification of the relative toxicity of substances in an aqueous medium, i.e., of water-soluble substances, but also of substances which, with the aid of dissolving intermediaries such as, e.g., acetone, can be rendered water-soluble. At the same time, it also provides information about the toxic effects, on the water fauna, of substances, in particular of insecticides and pesticides.

By means of periodical measurements over identical time intervals and with rising concentrations of the toxic doses, it is possible to prepare characteristic lethal-dose curves which permit conclusions to be drawn concerning the type of the toxic substance, and which contribute to an exploration of the effective mechanism of the substance or the substance combination.

BRIEF DESCRIPTION OF THE DRAWINGS

In the following, embodiments of the invention are explained in greater detail with the aid of drawings, in which

FIG. 12 is an actions/time diagram indicating the preparation, performance and evaluation of the measurement of the mobility of test organisms;

FIG. 13 shows the measurement of up to 6 titration trays according to the diagram of FIG. 12;

FIG. 14 represents the measurement of up to 10 trays, with a period of time of up to 10 minutes being allowed for each tray;

FIG. 15 shows the sequential course of single measurements, represented within the time interval of the measurement of a tray;

DETAILED DESCRIPTION OF THE INVENTION

Figure 1:
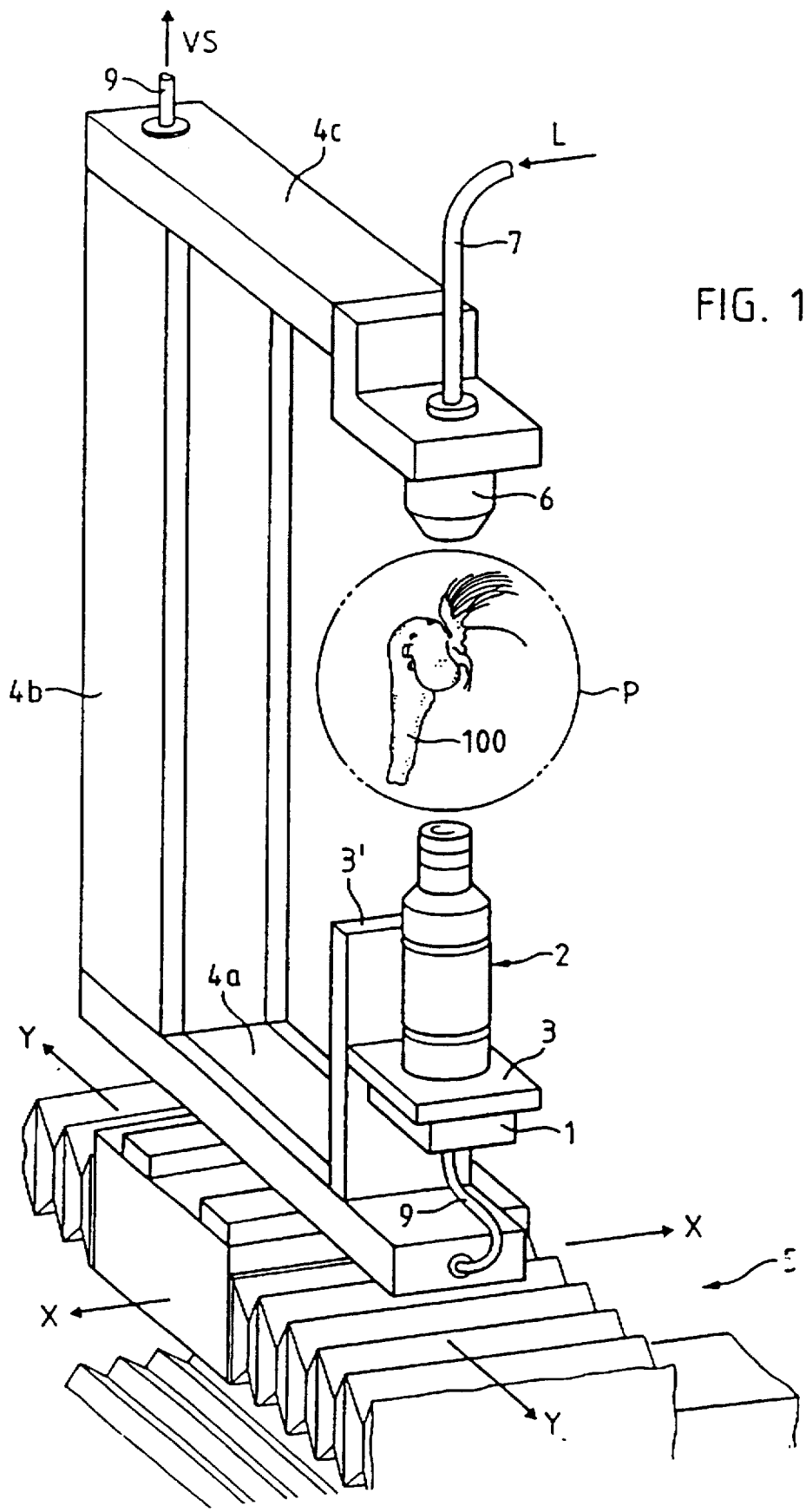
FIG. 1 is a schematic representation of an electrooptical image acquisition unit with a characteristic test organism for the determination of the mobility thereof.

Designated with numeral 1 in FIG. 1, there is seen a video camera (CCD-Shutter Camera, Sony Type XC-77 RR-CEO. The optics 2, mounted on electronic camera 1 is a macro-objective (Sony Type CM 50). Video camera 1 is arranged vertically in a per se known manner on two supports 3, 3' attached to a C-arm 4a–4c. The C-arm rests on a commercially available positioning unit 5, an XY-table with two feeding units (ISEL Automation D-6419 Eiterfeld), comprising appropriate stepping motors permitting displacement, in the X-direction, of 400 mm, and of 300 mm in the Y-direction.

Between optics 2 and light diffuser 6, there are located samples P, characterized by an Artemia salina 100, observed in transmitted light.

Vertically above optics 2, there is located on the C-arm a light diffuser 6 which is fed from a light source not shown, by a light guide 7. Via signal leads 9, the video signals VS are led upwards (see also FIG. 3, FIG. 4).

Figure 2:
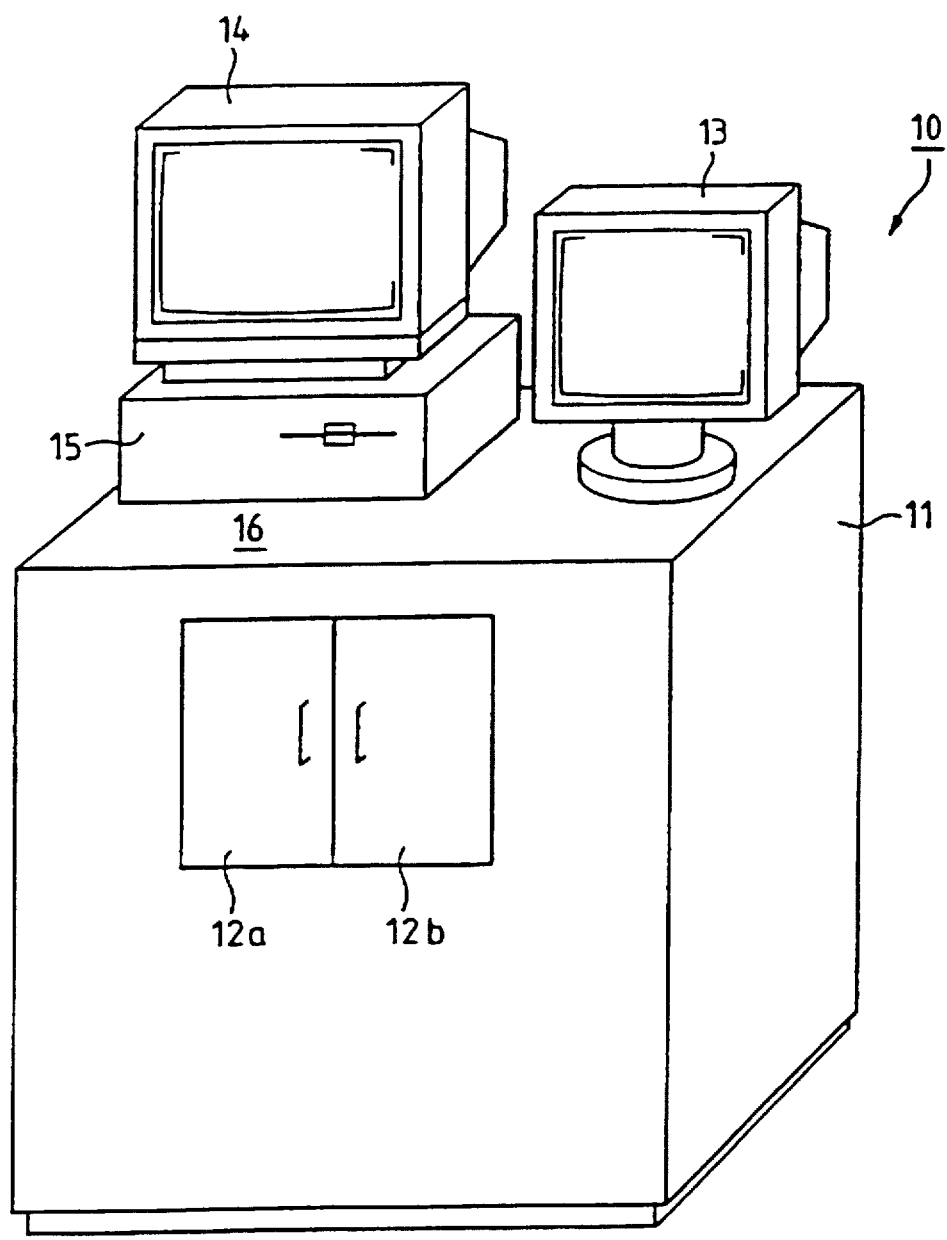
FIG. 2 represents a general view of an apparatus including the image acquisition unit and an evaluation arrangement.

The entire device for the observation and evaluation of test organisms is comprised in an image acquisition and evaluation unit 10, 10', in FIG. 2 designated 10. Two doors 12a, 12b in an instrument cabinet 11 permit a sample space to be supplied with specimens. On top of cabinet 11 there is located a commercial central processing unit 15 of a personal computer (PC), including an equally commercial monitor 14. Adjacent to the PC there is disposed on a rotatable mount a further monitor 13 which displays the images taken by the video camera located in cabinet 11. On cabinet 11 there is provided a depositing surface 16 for the operating and input devices (keyboard, mouse) not shown, but required for operating the device.

Figure 3:
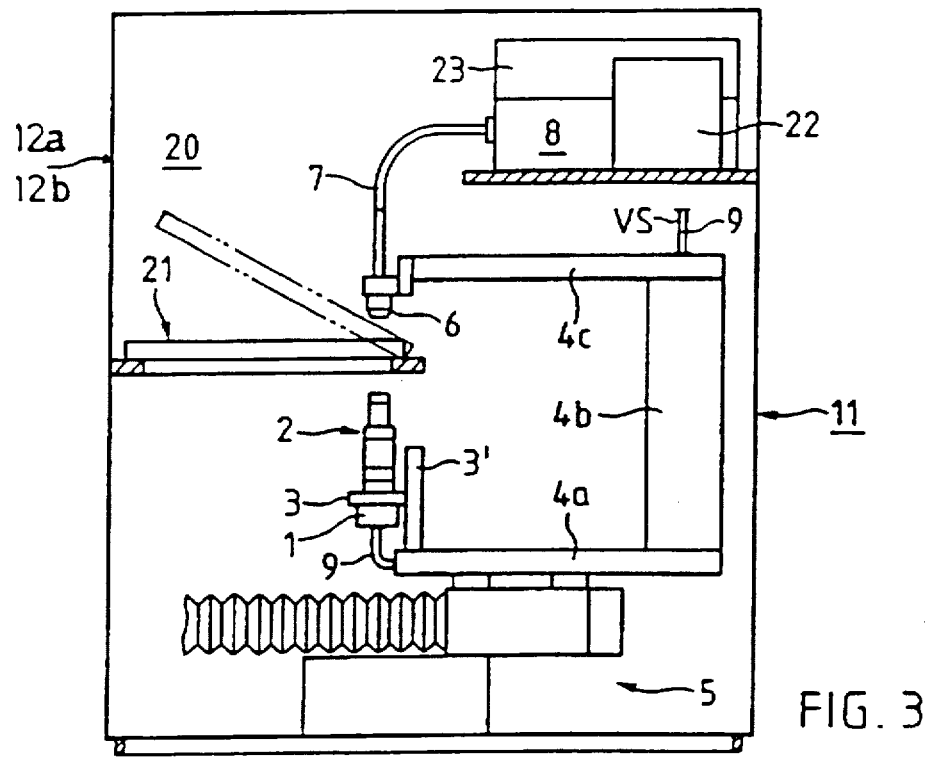
FIG. 3 is a partial cross section through the instrument cabinet of FIG. 2, in a direction perpendicular to the front panel.

The sectional view of FIG. 3 shows the inside of the instrument cabinet, the orientation of the section being given by the position of doors 12a, 12b. Seen again is C-arm 4a, 4b, 4c with its components, FIG. 1, as well as positioning unit 5 and light guide 7, which is connected to a conventional light source 8.

Figure 4:
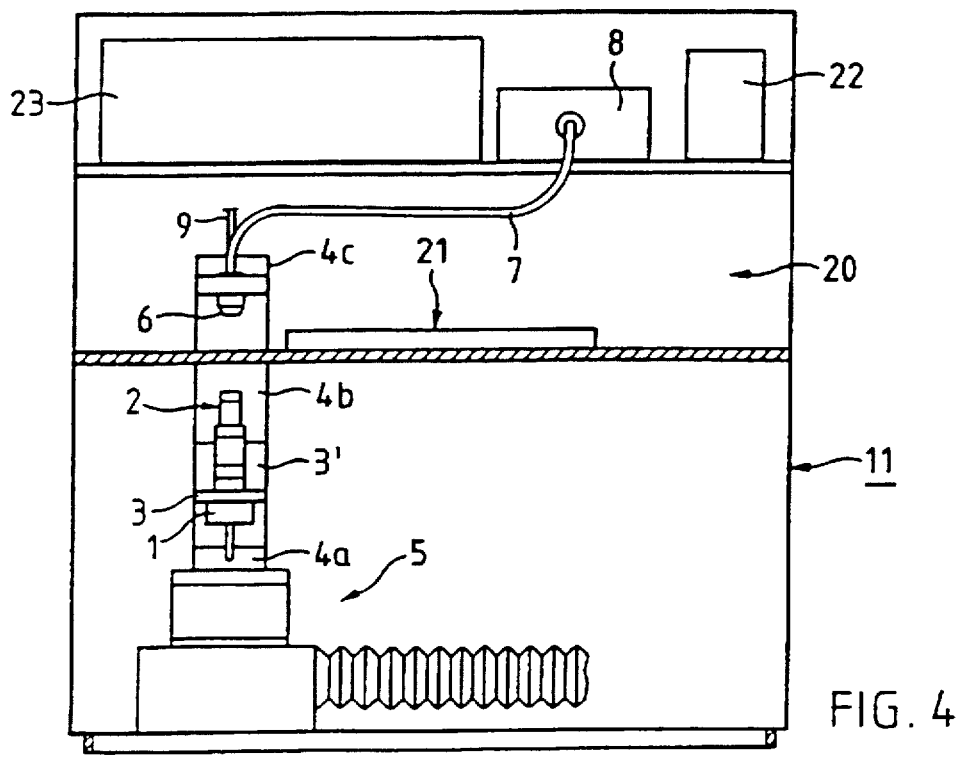
FIG. 4 represents a partial cross section through the instrument cabinet of FIG. 2, in a direction parallel to the front panel.

In a sample space 20, accessible via doors 12a, 12b, there is located a titration tray arrangement 21, which accepts samples with test organisms. Power to the entire device is provided by a commercially available non-break power supply 22. FIGS. 3 and 4. All signals required for the control of positioning unit 5 are generated in control unit 23. Video signals VS are led to a conventional camera control unit in control computer 15.

Not shown are the per se known peripherals such as printers, plotters, etc., which are connectable to the PC.

Figure 5:
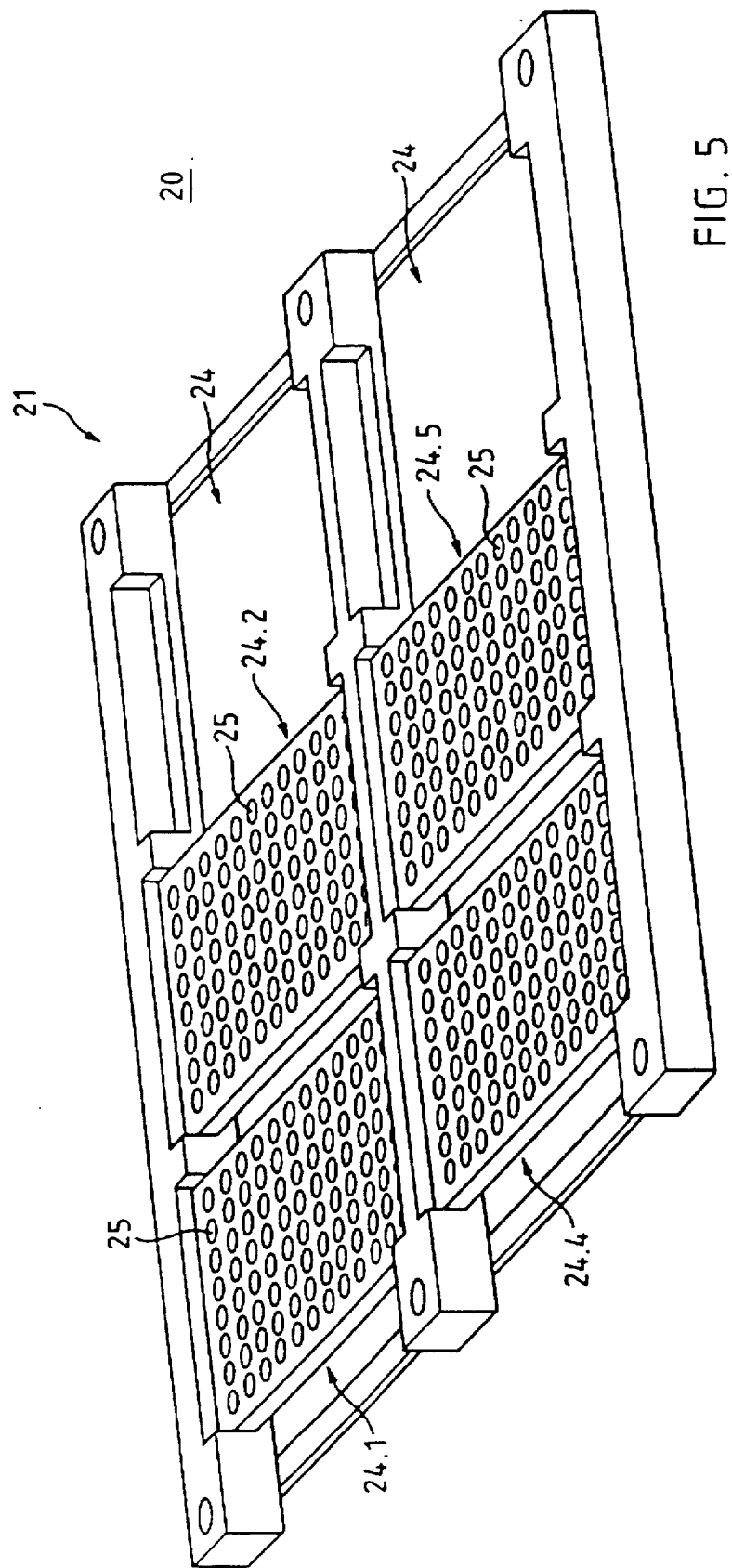
FIG. 5 shows a titration tray arrangement for accommodation of six sample trays.

FIG. 5 represents titration tray arrangement 21 located in sample space 20 and including its most essential components.

Arrangement 21 consists of a frame fixedly attached to cabinet 11 and having openings 24 into which can be introduced six micro-titration trays 24.1–24.6, each having 96 receptacles, each receptacle containing one test organism sample (about 12 Artemia salina). A protective cover (not shown) prevents interference with the samples by dust effect and/or heat radiation, etc. Furthermore, the separate titration trays are covered with a transparent plastic material, to reduce the evaporation effect.

Using the above-described device, mobility of the test organisms can be measured. In the simplest manner, this is effected by determining the locomotion velocity of the organisms in a test solution, the relative velocity relating to a control solution (without a toxic substance).

Planning a test series, the user is best guided by a PC-program. The latter inquires as to the number of concentrations (in mol or percent) and parallel determinations, blind values, controls and their arrangement, as well as the placing of the specimens in the respective receptacles of the multi-receptacle arrangement. Furthermore, the program requires data concerning the name of the test substance, its molecular weight, the highest concentration to be tested and the choice of the linear or logarithmic dilution series. After having received the information concerning the total volume for the test, the volume into which the test organisms (for example, Artemia salina) as well as the test substance are added, the program calculates the volume of the test substance required for the test. After weighing-in of the quantity, the required dilution can be effected under the guidance of the program. Pipette-assisted admixture is facilitated with the aid of optical means on the monitor screen.

A preferred sea-water solution contains 2800 mg NaCl, 342 mg $MgSO_4.7H_2O$, 234 mg $MgCl_2.6\ H_2O$, 122 mg $CaCl_2.2H_2O$, 20 mg $NaHCO_3$, 74 mg KCL, for 100 mg distilled water.

In a first step, by electrooptical determination, the number of test organisms is determined which are present in the artificial sea-water solution to which the substance to be tested has been added.

Observation of the effect of the substance on the organisms takes place at predetermined points of time with the aid of the present image analysis system an d permits the determination of the following:

Number of organisms;
How many of them are no longer active;
Average mobility or relative movement velocity, resp.;
Average size (relative surface area) of the organisms; their individual, position-dependent surface-area centroid.

The electrooptical determination is in principle carried out as follows:

In the micro-titration tray containing the test substance, the samples are placed into the automatic analyzer described. At the predetermined measurement instants, an electronic camera moves below the separate measurement locations of the titration tray and takes 12 to 36 images. At the same time, the respective sample is illuminated from above. For these images to be sharp, one must work with a camera with exposure control. The objective of this camera is so designed that, on the one hand, the image will fill the frame and, on the other, that the image will be sharp over the entire depth of the liquid (about 1 cm). Illumination is effected via a light guide which, attached to the C-arm, travels together with the camera. Resolution was so optimized that the entire analysis could be carried out with a minimum of pixels. This permitted to keep the calculation time for the image analysis as low as possible. The resolution selected was 256 times 256 pixels. With this resolution, the outlines of the organisms could still clearly be discerned. Due to this, a measurement and evaluation period of about three minutes was achieved per titration tray (with 96 receptacles), i.e., approximately 2 seconds per measurement location.

At the conclusion of measurements, the data are stored on a floppy disk and may now be directly evaluated with the aid of a PC-program. In addition, the data are graphically represented and the characteristic toxicity values directly ascertained. These data are then stored in a data bank, so that they are always available for purpose of comparison.

For carrying out the above automated analysis of liquid samples, micro-titration trays are used made of transparent material. By means of a multi-receptacle arrangement consisting of two materials having differing physical properties, it is possible to adjust the surface tension of the liquid surface to such effect that the latter is at least approximately planar. This is achieved by preferably making the bottoms of the multi-receptacle arrangement of a transparent material U.S. Pat. No. 5,540,891, e.g., polystyrene or a copolymer of a polystyrene, and the walls of a less light-transmissive material, e.g., polyolefines or polytetrafluoroethylene, which do not cause meniscus formation or protein adsorption.

Figure 6:
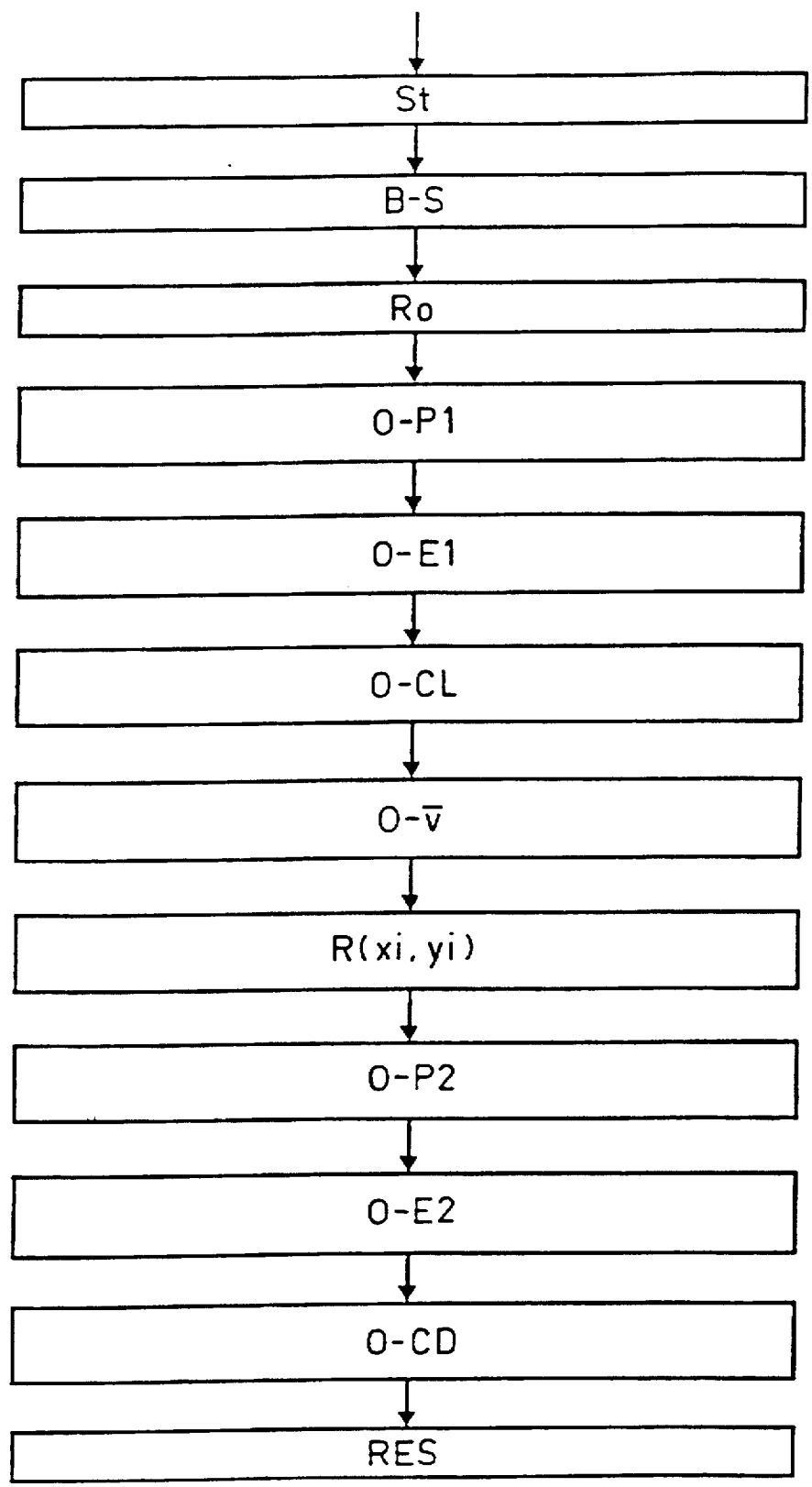
FIG. 6 is a flow diagram showing the course of the program for the automated determination of the mobility of test organisms.

The above schematized, practically tested program course in the device according to FIGS. 1 to 5 can be followed in the representation of FIG. 6, in which the start is designated St and the program end, RES=Result.

After start, the sequence of images is taken on-line at constant time intervals $\Delta t$, the values being binarized in a per se known manner and are stored in a buffer memory: designated B-S.

Subsequently, the measurement-window radius is determined, dependent on the liquid level: designated Ro.

In a further step, the objects are characterized and the object parameters of all images within the measurement window are determined, i.e., the centroid coordinates, the relative surface area, the circumference and number of visually (electronically) identifiable holes in the object in each receptacle are measured for identification: O-P1.

After that, inadmissible objects in all images are eliminated, with the criterion being programmed by admissible magnitudes of surface area and circumference: O-E1.

Now, the number of test organisms per sequence for all image data is determined and designated O-CL=Object Counting. This corresponds to the total number of living organisms per image.

By measuring the velocity of the organisms from all previously determined image data, a mean value is formed. In FIG. 6, this value is designated $O\text{-}\bar{v}$= mean velocity of the organisms, with the instantaneous coordinate of the surface area centroid in the organism silhouette serving as measurement reference.

Subsequently, an image is produced of the result as based on pixels with the coordinates xi, yi and normalized in such a way that the numeral 1 will stand for a nonmoving, dead object. The rest of the pixels xi, yi are set at zero (=0). This method step is designated R(xi, yi).

Under O-P2, the objects are again characterized and the object parameters of all images within the measurement window are determined, i.e., the centroid coordinates, the relative surface area, the circumference and the number of objects in the receptacle are measured.

After that, inadmissible objects in all images are again eliminated, with the criterion being programmed by admissible magnitudes of surface area and circumference: O-E2.

After that, the residual, dead objects in the result image are counted: O-CD.

Under RES, the evaluation of the results takes place, using statistical methods in a per se known manner (Probit, etc.)

Figure 7:
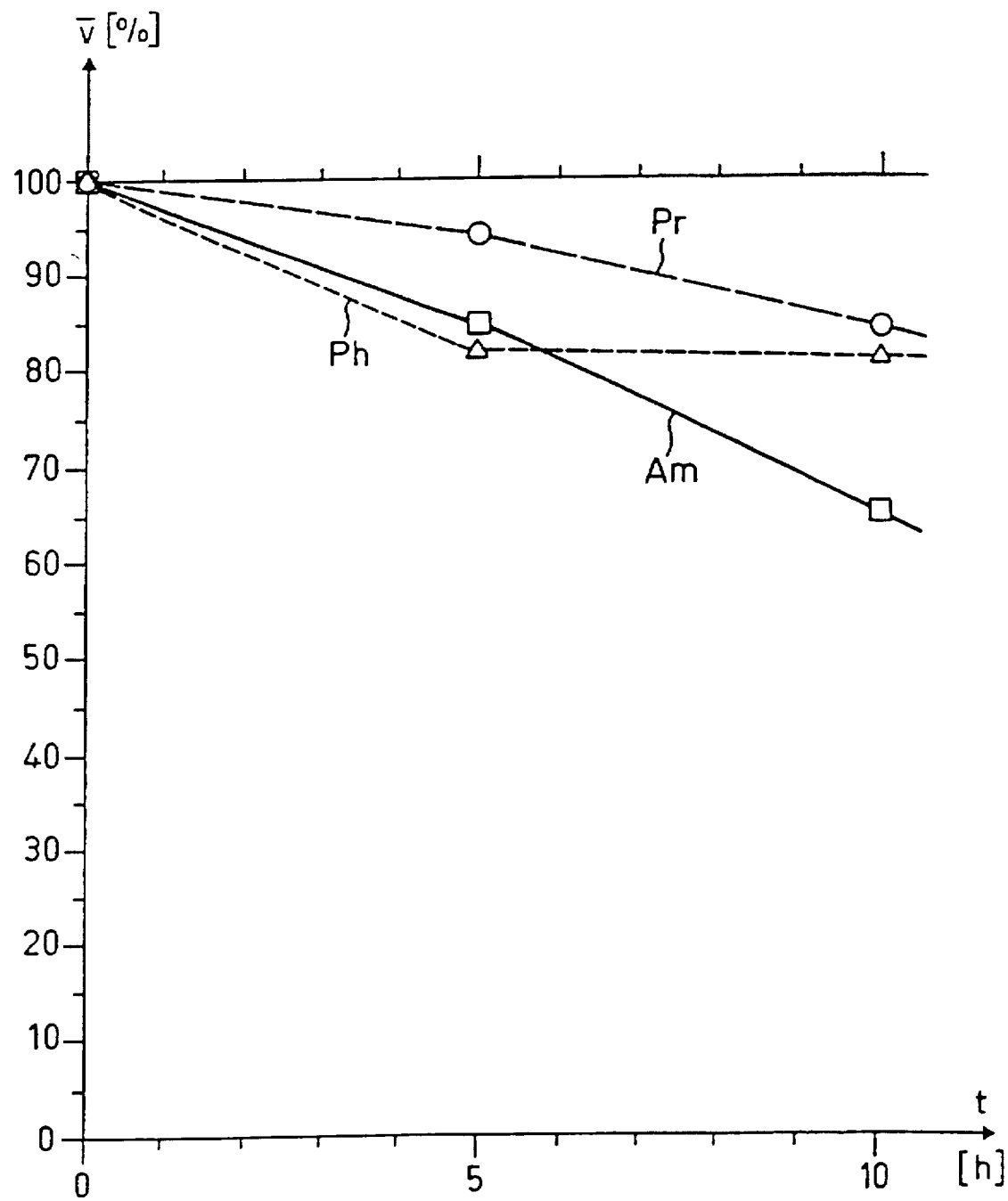
FIG. 7 represents a characteristic mean velocity decrease, as a function of time, of living organisms in three selected toxic solutions, as observed over a period of time of 10 hours.

As seen in FIG. 7, with three known, selected solutions, those containing phenobarbital are designated Ph, amphetamine sulfate-Am and D-propoxyphene-Pr. The shift of location per unit time of Artemia salina was determined and recorded as mean velocity v.

In a control solution, i.e., in a solution of artificial sea-water described further below, typical mean velocities of the Artemia salina were established of $5 \cdot 10^{-3}$ m/s up to $6 \cdot 10^{-3}$ m/s.

As emerges from the representation of FIG. 7, in the case of D-propoxyphene, a relatively linear drop in velocity takes place over a period of 10 hours to about 65% of the initial velocity, and in the case of phenobarbital, to about 80%.

It was shown that, depending on the toxicity equivalence factor (type or group or class of the toxic substance), characteristic velocity decreases could be perceived. This can be generalized to cover also significant and thus detection-promoting effects of separate substances and combination of substances.

Depending on the nature of the effect of the substance on the organism, the significance of the measurements can be optimized by a suitable image evaluation and by an adaptation of the measurement method. For instance, instead of observing the locomotion velocity, it is possible to observe the specific mobility of separate organs of the organism. Besides, by forming the first derivative from the velocity measurement, cyclic movements can be emphasized and more readily recorded and analyzed.

Practical example concerning the determination of toxicity of Paraoxone

Figure 8:
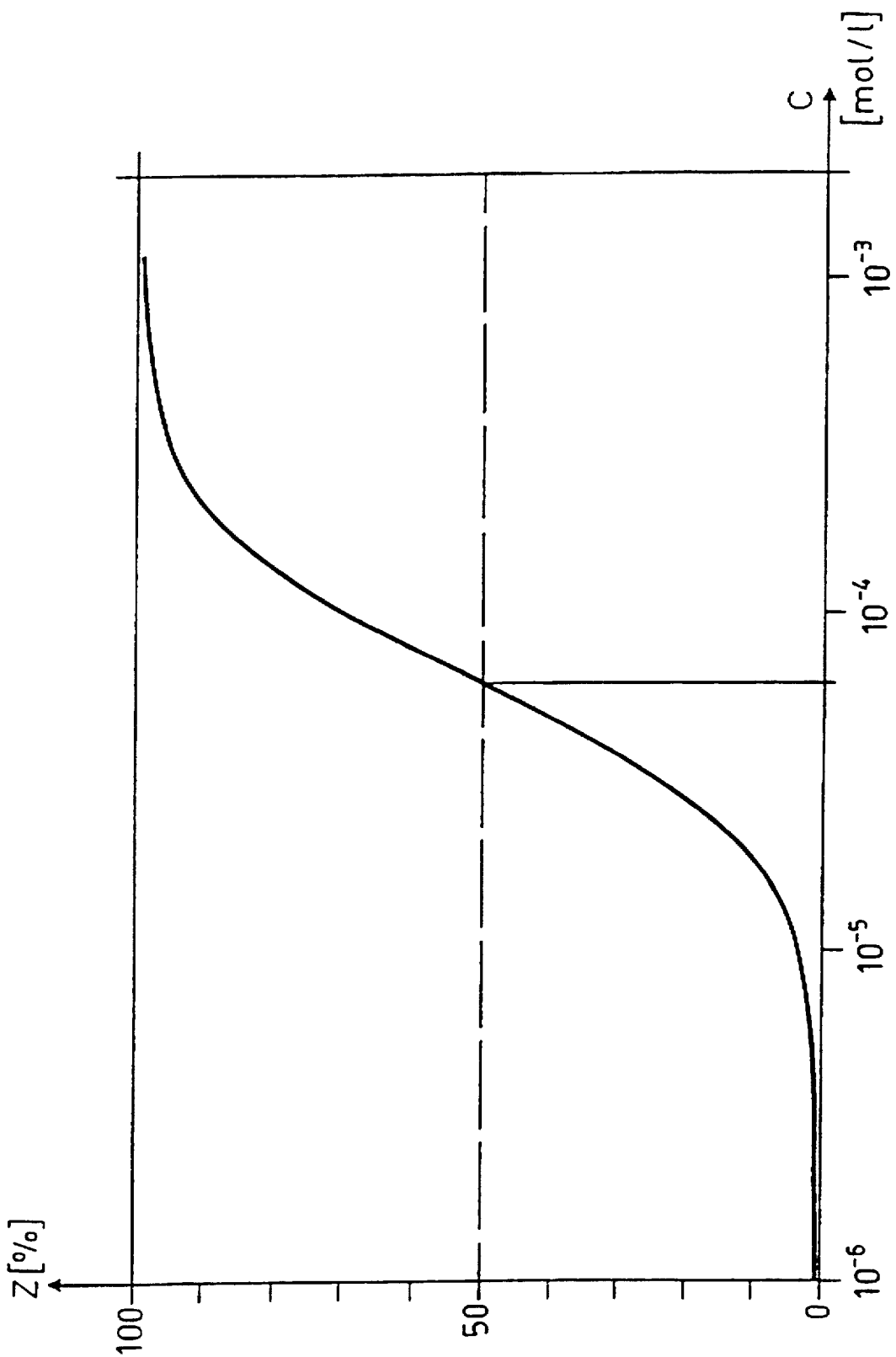
FIG. 8 illustrates a toxicity test with Artemia salina in a Paraoxone solution, with the abscissa representing the concentration and the ordinate the proportion of dead organisms.

In FIG. 8, the proportion Z of dead organisms relates to 100% at the beginning of the measurement. With increasing concentration C of Paraoxone, an increase of Z is perceived. This type of evaluation permits the establishing of the well-known $LC_{50}$-value of toxic substances.

The calculation of the number of dead Artemia salina is based on the measurement, according to the above described method, of the velocity of the test organisms, with an observed velocity zero indicating a dead organism.

The curve shown in FIG. 8 is a mean value derived from four independent test series covering a concentration range of Paraoxone in artificial sea-water over three orders of magnitude. The mean value of the thus determined $LC_{50}$-values at a temperature of 22° C. is $5.9 \cdot 10^{-5}$ at a maximum dispersion of 33%.

Figure 9:
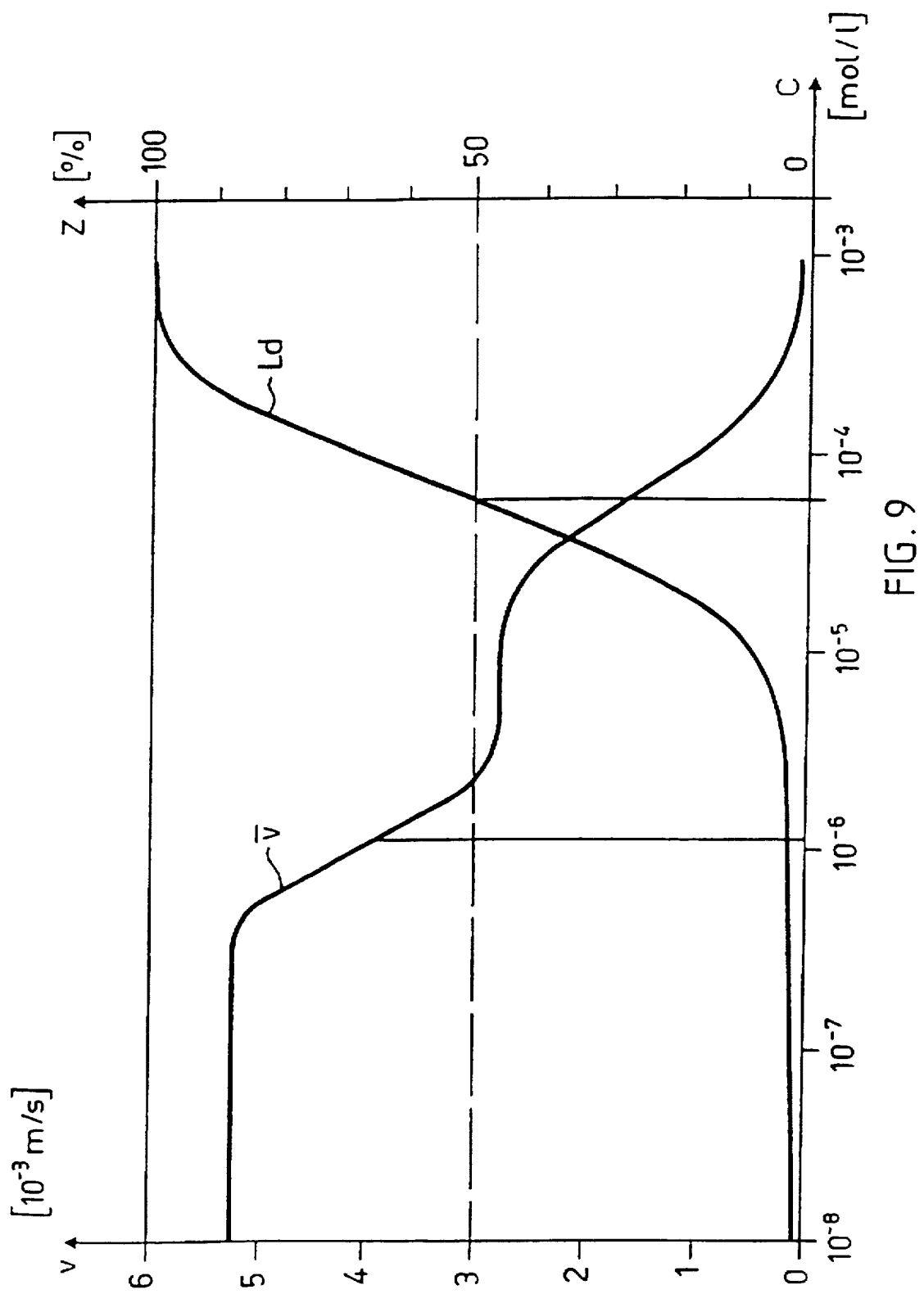
FIG. 9 shows a further toxicity test, with the velocity of the test organisms being represented as a function of the Paraoxone concentration, together with a superposed lethal-dose curve.

FIG. 9 shows the velocity $\bar{v}$ of the Artemia salina test organisms in a test series as measured 30 min after admixture of the Paraoxone solutions with increasing concentrations. Two drastic drops in velocity can be observed. The second drop, at about $1 \cdot 10^{-4}$ mol/l Paraoxone corresponds to the $LC_{50}$-value as can be inferred from the superposed lethal-dose curve.

The significant first drop in velocity occurs at about $1 \cdot 10^{-6}$ mol/l Paraoxone and corresponds to the "Effect Concentration" $EC_{50}$. The latter serves as an indication of the function of the toxic substance.

Figure 10:
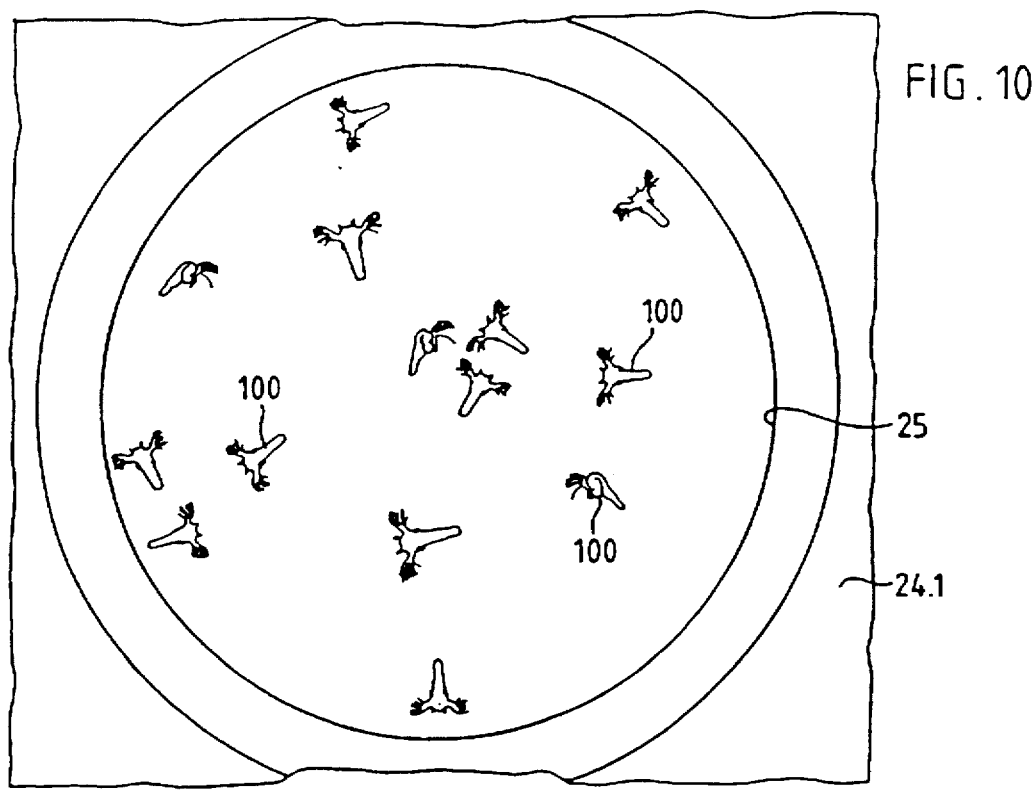
FIG. 10 represents a video image of a group of living test organisms in an aqueous medium at the beginning of the observation.
Figure 11:
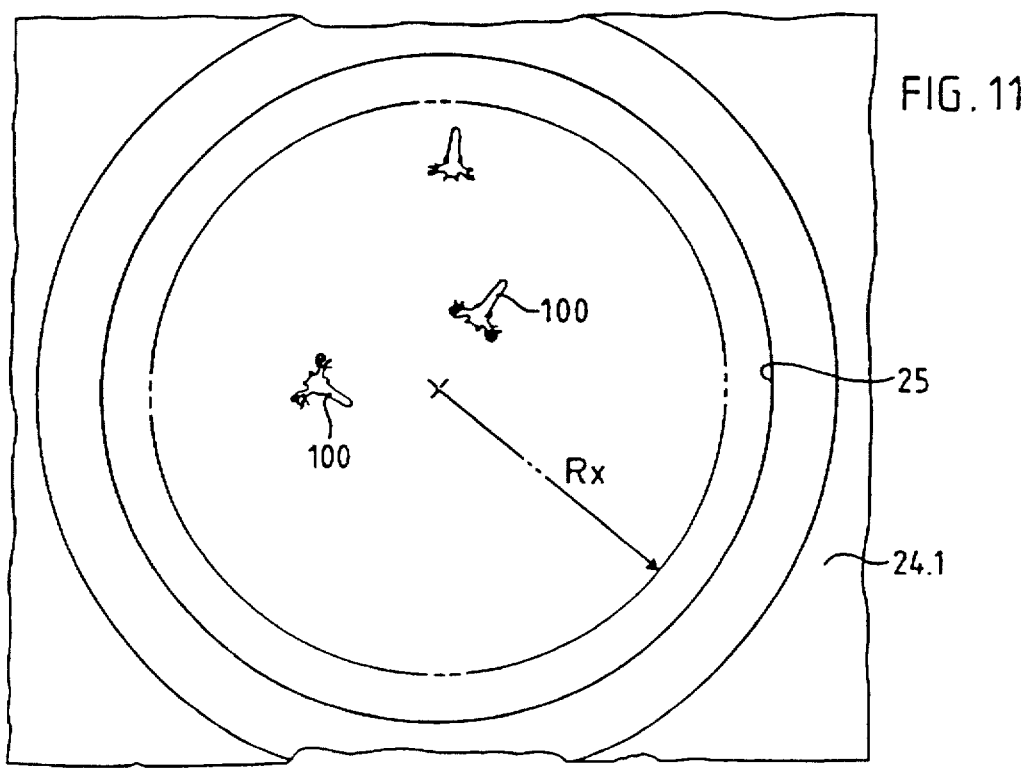
FIG. 11 is a further video image of the group of still living test organisms of FIG. 10 after 24 hours, with part of the medium evaporated.

Characteristic video images can be seen in FIG. 10 (at the beginning of the experiment) and FIG. 11 (at the conclusion of the experiment after 24 hours).In the second image, the dead, i.e. nonmoving, animals have been electronically suppressed in a per se known manner and are therefore invisible on monitor 13, FIG. 2.

FIG. 11 shows an additional radius Rx which indicates possible evaporation of liquid and the resulting reduction of the measuring window radius; drawn in a dash-dotted line.

Further details of the technical method course can be gathered from FIGS. 12–17, with the action/time diagram showing the entire course of the method. In its separate steps, this diagram is designated with I–V, the order of magnitude of the duration of the method steps being marked on the abscissa.

The numerals stand for:

I Preparation of the measurement series, aided by a "Setup Help" on the PC for loading the titration trays;

II Calibration of the start values of the monitoring program;

III Admixing of the toxic substance;

IV "Shooting" (taking) the measurement series with the aid of the monitoring program;

V Evaluation of the measurement series using statistical methods of analysis and correlations with previous measurements (data bank).

Subsequent FIGS. 13 to 17 relate all to method step IV, as marked for clarity on all these action/time diagrams.

FIG. 13 represents the typical course during the shooting of a measurement series of up to six titration trays, measurement taking place in hourly intervals. This series corresponds to position IV in FIG. 12.

In FIG. 14, position IV ("shooting" of the measurement series) is resolved in detail. The separate titration trays are designated P1 01–P1 06, with the maximum measurement duration is actually limited to 10 minutes.

The separate method steps during the measuring period can be derived from FIG. 15. Here are designating:

a1 the establishing of a binarization threshold for image processing;

a2 the adjusting and checking of the camera focussing by means of image processing;

a3 the checking of titration tray orientation (for setting, and allowing for, the diminishing concentration values of the samples);

a4 the measurement of a first receptacle;

a5–a7 the measurement of any or of the n-th receptacle.

Figure 16:
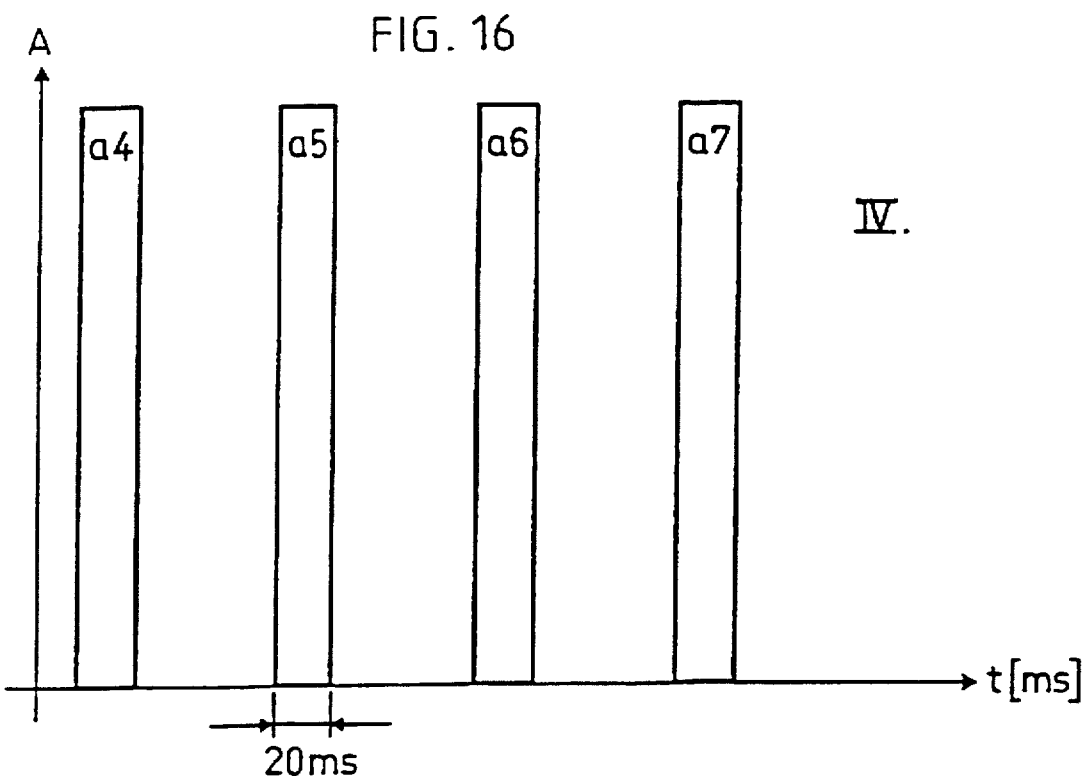
FIG. 16 shows the intervals provided for measurement of a single receptacle, the time intervals between the single measurements being determined by the transport mechanism of the camera.

FIG. 16 represents the sequential taking of pictures per receptacle, for which, in practice, a maximum time interval of 20 ms is provided.

Figure 17:
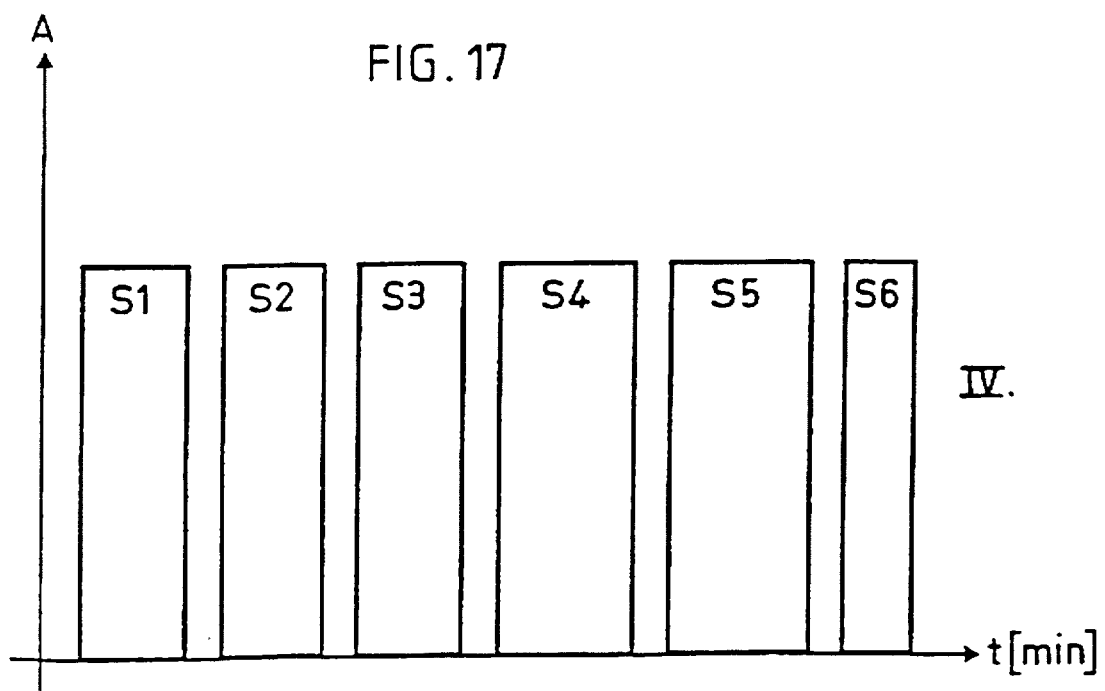
FIG. 17 represents a sequential evaluation of all method courses required to assessably register a single receptacle in a titration tray.

FIG. 17 illustrates the sequence evaluation, with S1 standing for the evaluatable radius of the receptacle, S2 signifies the centroid coordinates in image 1 and the centroid coordinates of an organisms in image n, which are determined by image processing.

In the following step, designated S4, the number of organisms and their mean velocity are established by calculation, using all image data.

The further sequences are S5, the combining of all images to form a resultant image which contains only dead organisms, and sequence S6, the counting of the dead organisms by means of image processing.

The investigations, largely conducted with toxic substances, can be generalized to include also threshold values, threshold stimulation, threshold doses and concentrations.

Besides, the use of micro-organisms makes possible a massive saving on experimental animals, as their number can be limited due to the preceding determination of the concentrations to be tested.

It is envisaged to apply the object of the invention also to further, not yet tested organisms such as Nematoda as well as other organisms also within the micro range.

The method can also be combined with conventional methods of analysis, enabling the measurement duration to be shortened and the validity of the measurements to be rendered still more authentic, without the need for expensive experimental series.

We claim:

1. A device for determination of the toxicity of substances soluble in, or miscible with, water, by analysis of aqueous medium test samples having aquatic test organisms of a microscopically-observable scale, comprising means for performing at least one reference measurement on a first test sample without a toxic substance and at least one further measurement on at least one additional test sample having an admixture of the toxic substance by the electrooptic observation of the movement activity of the test organisms as observed in at least one plane, wherein said device comprises: (a) an image acquisition unit for carrying out object recognition in a field of at least one plane wherein said field extends substantially across a test sample and wherein object parameters are determined at predetermined time intervals in the test sample by the development of electronic images bearing information corresponding to recognized objects with selected object parameters appearing within the field, said image acquisition unit further comprising means for locating and identifying said test organisms from among the recognized objects and sequentially recording the positions of the test organisms at the predetermined time intervals, and an evaluation apparatus including a computer and display devices coupled to said image acquisition unit for carrying out a statistical evaluation of at least one of the viability, mobility and size of the test organisms and correlating results obtained with levels of the toxic substance in the test samples.

2. The device according to claim 1, wherein the image acquisition unit comprises means for generating a gray-scale image of at least one group of test organisms extant under the same conditions, the evaluation apparatus comprising means for establishing binary black/white values from the gray-scale image and for performing sequential single-image evaluations of instantaneous coordinate positions of the test organisms, and for calculating a relative measure of at least one of the mobility, size and number of the test organisms by comparison with an earlier taken image and reference to the time interval between said images.

3. The device according to claim 1 wherein said evaluation apparatus comprises means for marking recognized objects in an image which are not test organisms and which have a relative mobility of zero and for deleting such marked objects from further computational processing.

4. The device according to claim 1 wherein the image acquisition unit comprises a single CCD-shutter camera and means for guiding said camera in an identical step-wise manner over the test samples.

5. The device according to claim 1, wherein the image acquisition unit comprises two CCD-shutter cameras, the respective optical axes of which form at least an acute angle with respect to each other detecting the movement and/or size of the test organisms in three dimensions.

6. The device according to claim 1, wherein the image acquisition unit is stationary, further comprising means for sequentially passing said test samples past said image acquisition unit at a constant velocity for analysis.

7. The device according to claim 6, wherein said passing means comprise means for arranging the test samples in a circular formation.

* * * * *